United States Patent
Lankton

(12) 
(10) Patent No.: US 6,376,735 B1
(45) Date of Patent: Apr. 23, 2002

(54) PROCESS TO REMOVE REACTION BY-PRODUCTS FROM A SELECTIVE HYDROGENATION EFFLUENT STREAM

(75) Inventor: Steven P. Lankton, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/739,606

(22) Filed: Dec. 19, 2000

(51) Int. Cl.⁷ .............................. C07C 5/08; C07C 5/03; C07C 7/00
(52) U.S. Cl. ................... 585/809; 585/810; 585/259; 585/264; 585/285; 208/308
(58) Field of Search .................. 585/809, 810, 585/264, 285, 259; 208/308

(56) References Cited

U.S. PATENT DOCUMENTS 4,049,742 A * 9/1977 Weitz et al. .......... 260/681.5 R
5,154,802 A * 10/1992 Lee et al. .................. 203/51

\* cited by examiner

*Primary Examiner*—Walter D. Griffin
*Assistant Examiner*—Tam M. Nguyen
(74) *Attorney, Agent, or Firm*—John G. Tolomei; John G. Cutts, Jr.

(57) ABSTRACT

A process for the rejection of heavy reaction by-products from a selective hydrogenation reaction zone effluent containing butadiene and trace amounts of heavy reaction by-products by introducing the selective hydrogenation reaction zone effluent into a butadiene extraction vaporizer containing a fractionation zone, refluxing the fractionation zone with a raffinate stream from a butadiene extraction zone; removing a vaporized stream containing butadiene and having a reduced concentration of heavy reaction by-products from the vaporizer; removing and recovering a concentrated liquid product stream containing heavy reaction by-products from the vaporizer; and introducing the vaporized stream containing butadiene into the butadiene extraction zone.

5 Claims, 1 Drawing Sheet

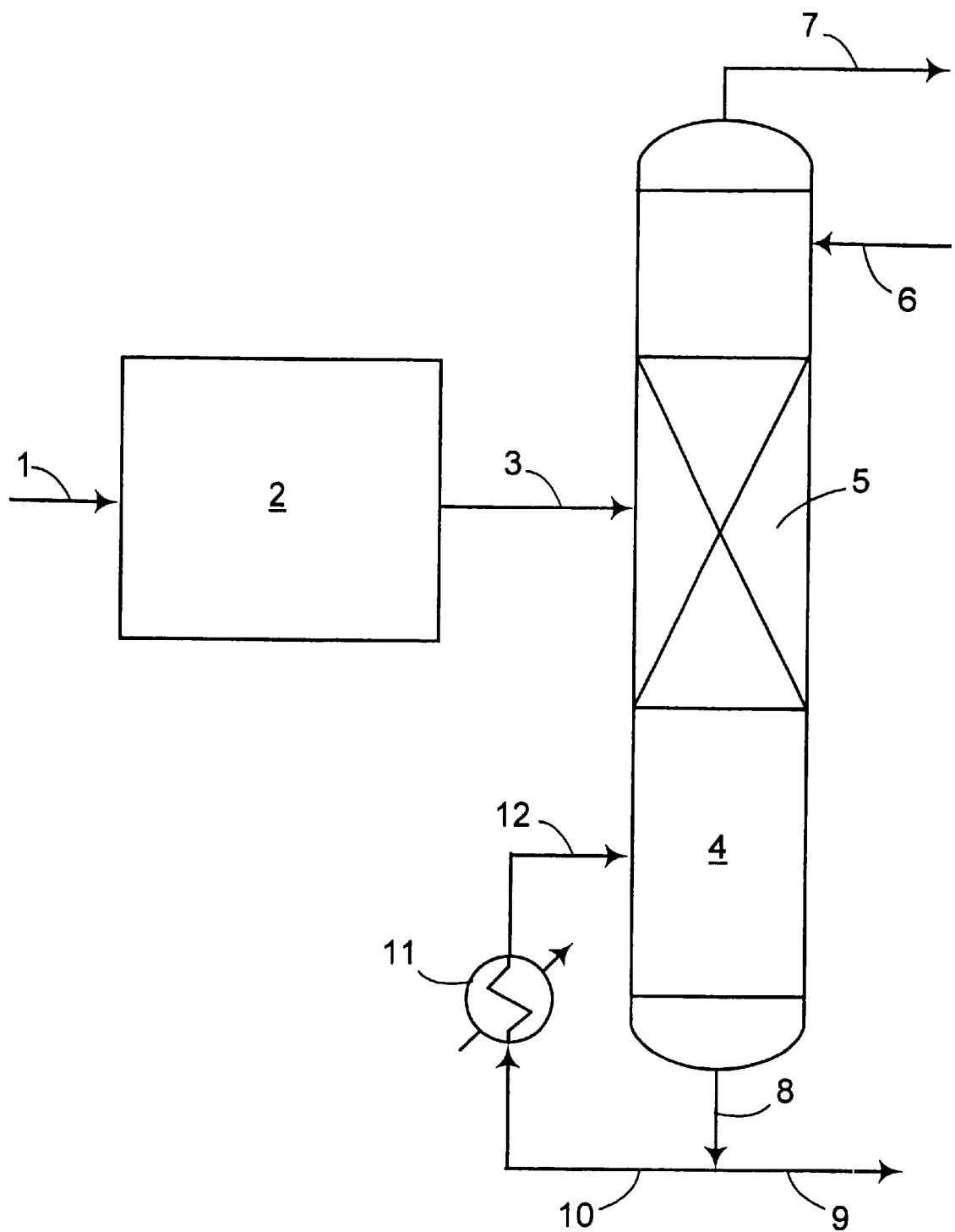

PROCESS TO REMOVE REACTION BY-PRODUCTS FROM A SELECTIVE HYDROGENATION EFFLUENT STREAM

BACKGROUND OF THE INVENTION

The field of art to which this invention pertains is the removal of high molecular weight reaction by-products from a selective hydrogenation reaction zone effluent.

INFORMATION DISCLOSURE

Processes for the production, recovery and purification of butadiene are known and butadiene is useful for the production of synthetic rubber. Crude butadiene streams are produced from the thermal and catalytic cracking of hydrocarbons. The production of crude butadiene streams also produces undesirable co-products such as ethyl acetylene and vinyl acetylene, for example. The explosive nature of the acetylenes and their tendency to form and deposit polymers calls for special precautions when handling the hydrocarbon stream containing acetylene. In addition, when a butadiene-rich stream is used for the production of synthetic rubber, the presence of acetylene is highly undesirable and must be removed. In order to minimize and reduce the difficulties presented by the presence of acetylenes, the crude butadiene streams are selectively hydrogenated in a selective hydrogenation zone operated to convert the acetylene to diolefins. However, the selective hydrogenation of acetylene produces trace quantities of heavy reaction by-products commonly referred to as polymers or "green oil". In a stand alone selective hydrogenation process for the hydrogenation of acetylenes, the co-produced green oil was removed from the desired butadiene steam by means of a fractionation column having all of the conventional components including a reboiler, overhead condenser and receiver, and a reflux pump.

U.S. Pat. No. 4,049,742 (Weitz et al) discloses a process wherein 1,3-butadiene is recovered with the aid of a selective solvent from a $C_4$ hydrocarbon mixture containing 1,3-butadiene, hydrocarbons which are more soluble in the selective solvent than 1,3-butadiene, including acetylenes and possibly 1,2-butadiene and $C_5$ hydrocarbons, and hydrocarbons which are less soluble in the selective solvent than 1,3-butadiene. The crude $C_4$ hydrocarbon mixture is separated by the use of one or more extractive distilling zones into a distillate containing the less soluble hydrocarbons, a stream consisting of 1,3-butadiene and a stream containing the more soluble hydrocarbons including the higher acetylenes and 1,3-butadiene.

In accordance with the present invention, it has been discovered that when the liquid effluent from a selective hydrogenation reaction zone containing crude butadiene and trace amounts of heavy reaction by-products is vaporized in preparation for subsequent extraction of butadiene in a selective solvent process, a stream rich in heavy reaction by-products is isolated and recovered. The present invention utilizes a vaporizer containing a fractionation zone which is refluxed with a liquid raffinate process stream from the solvent extraction zone.

BRIEF SUMMARY OF THE INVENTION

It has now been found that an improved process for the rejection of heavy reaction by-products from a selective hydrogenation reaction zone effluent can be achieved by introducing the selective hydrogenation effluent into a butadiene extraction vaporizer containing a fractionation zone which is refluxed with a raffinate stream from the butadiene extraction zone. This produces a vaporized stream containing butadiene and having a reduced concentration of heavy reaction by-products, and a concentrated liquid product stream containing heavy reaction by-products.

One embodiment of the present invention is a process for the rejection of heavy reaction by-products from a selective hydrogenation reaction zone effluent containing butadiene and trace amounts of heavy reaction by-products which process comprises: (a) introducing the selective hydrogenation reaction zone effluent into a butadiene extraction vaporizer containing a fractionation zone; (b) refluxing the fractionation zone with a raffinate stream from a butadiene extraction zone; (c) removing a vaporized stream containing butadiene and having a reduced concentration of heavy reaction by-products from the vaporizer; (d) removing and recovering a concentrated liquid product stream containing heavy reaction by-products from the vaporizer; and (e) introducing the vaporized stream containing butadiene into the butadiene extraction zone.

Other embodiments of the present invention encompass further details such as fractionation zone details and operating conditions.

BRIEF DESCRIPTION OF THE DRAWING

The drawing is a simplified process flow diagram of a preferred embodiment of the present invention. The drawing is intended to be schematically illustrative of the present invention and not be a limitation thereof.

DETAILED DESCRIPTION OF THE INVENTION

The feedstock to the process of the present invention is the effluent from a selective hydrogenation reaction zone effluent containing butadiene and trace amounts of heavy reaction by-products. The feedstock is introduced into a butadiene extraction vaporizer containing a fractionation zone. The butadiene extraction vaporizer is preferably reboiled and the fractionation zone preferably contains from about 3 to about 7 theoretical stages. The vaporizer is preferably operated at conditions which include a temperature from about 80 to about 200° F. and a pressure from about 40 to about 100 psig.

The fractionation zone may contain any suitable elements such as random packing or any known fractionation trays. In accordance with the present invention, the fractionation zone preferably contains fractionation trays. The fractionation zone is preferably operated with a reflux to feed molar ratio from about 0.01 to about 0.02 and the concentrated liquid product stream containing heavy reaction by-products is removed and preferably recovered in an amount less than about 0.5 weight percent of the feedstock.

DETAILED DESCRIPTION OF THE DRAWING

In the drawing, the process of the present invention is illustrated by means of a simplified schematic flow diagram in which such details as pumps, instrumentation, heat-exchange and heat-recovery circuits, compressors and similar hardware have been deleted as being non-essential to an understanding of the techniques involved. The use of such miscellaneous equipment is well within the purview of one skilled in the art.

With reference now to the drawing, a crude $C_4$ feed stream and hydrogen is introduced into the process via line 1 and is introduced into selective hydrogenation zone 2. A selective hydrogenation zone effluent having a reduced concentration of acetylene compounds is removed from selective hydrogenation zone 2, transported via line 3 and introduced into butadiene extraction vaporizer 4 which contains fractionation zone 5. A raffinate stream from a butadiene extraction zone is introduced into butadiene extraction vaporizer 4 via line 6. A bottoms stream is removed from butadiene extraction vaporizer 4 via line 8 and a portion is transported via line 10 and introduced into heat-exchanger 11. The resulting heated effluent from heat-exchanger 11 is transported via line 12 and introduced into butadiene extraction vaporizer 4. At least another portion of the bottoms stream carried via line 8 is transported via line 9 and recovered. A vaporized stream containing butadiene and having a reduced concentration of heavy reaction by-products is removed from butadiene extraction vaporizer 4 via line 7 and introduced into a butadiene extraction zone.

The process of the present invention is further demonstrated by the following illustrative embodiment. This illustrative embodiment is, however, not presented to unduly limit the process of this invention, but to further illustrate the advantage of the hereinabove-described embodiment. The following data were not obtained by the actual performance of the present invention but are considered prospective and reasonably illustrative of the expected performance of the invention.

ILLUSTRATIVE EMBODIMENT

A crude $C_4$ feed stream in the amount and having the characteristics presented in Table 1 is introduced into a selective hydrogenation zone containing a selective hydrogenation catalyst containing copper. A hydrogen feed stream is also introduced into the selective hydrogenation zone at the rate of 11 kilograms per hour. The resulting effluent from the selective hydrogenation zone is introduced into a butadiene extraction vaporizer containing a fractionation zone. The fractionation zone is refluxed with a liquid raffinate stream from a butadiene extraction zone in the amount and having the characteristics presented in Table 1. A vaporized overhead product stream in an amount of 21,882 kg/hr and having the characteristics presented in Table 1 is recovered from the butadiene extraction vaporizer and introduced into the butadiene extraction zone. A bottoms stream containing heavy polymer compounds is removed from the butadiene extraction vaporizer in an amount of 54 kg/hr and recovered.

TABLE 1

MASS BALANCE (Kg/Hr)

| Component | Crude $C_4$ Feed | Hydrogen Feed | Raffinate Reflux to Vaporizer | Vaporizer Overhead Product | Vaporizer Bottoms Drag |
| --- | --- | --- | --- | --- | --- |
| Hydrogen | | 11 | | 1.6 | |
| Propane | 2.2 | | | 2.2 | |
| Propene | 6.5 | | | 15.6 | |
| Propadiene | 6.5 | | | 6.5 | |
| Methyl Acetylene | 8.7 | | | 0.02 | |
| i-Butane | 136.4 | | 4.5 | 145 | 0.1 |
| n-Butane | 482.9 | | 15.6 | 503.2 | 1.0 |
| 1-Butene | 3402.2 | | 112.0 | 3604.7 | 5.3 |
| i-Butene | 3989.1 | | 127.5 | 4107.3 | 5.3 |
| Cis-2-Butene | 913.9 | | 29.2 | 939.4 | 2.8 |
| Trans-2-Butene | 1124 | | 35.9 | 1156 | 2.7 |
| 1,3 Butadiene | 11317.6 | | | 11367.8 | 18.4 |
| 1,2 Butadiene | 6.5 | | 0.2 | 6.7 | |
| Ethyl Acetylene | 45.5 | | | 0.04 | |
| Vinyl Acetylene | 132.1 | | | 0.01 | |
| $C_5+$ | 26 | | | 25.4 | 0.6 |
| Green Oil | | | | 0.3 | 17.4 |
| Total, Kg/Hr | 21600 | 11 | 325 | 21882 | 54 |

The foregoing description, drawing and illustrative embodiment clearly illustrate the advantages encompassed by the process of the present innovation and the benefits to be afforded with the use thereof.

What is claimed:

1. A process for the rejection of heavy reaction by-products from a selective hydrogenation reaction zone effluent containing butadiene and trace amounts of heavy reaction by-products which process comprises:

(a) introducing the selective hydrogenation reaction zone effluent into a butadiene extraction vaporizer containing a fractionation zone;

(b) refluxing the fractionation zone with a raffinate stream from a butadiene extraction zone;

(c) removing a vaporized stream containing butadiene and having a reduced concentration of heavy reaction by-products from the vaporizer;

(d) removing and recovering a concentrated liquid product stream containing heavy reaction by-products from the vaporizer; and (e) introducing the vaporized stream containing butadiene into the butadiene extraction zone.

2. The process of claim 1 wherein the fractionation zone contains from about 3 to about 7 theoretical stages.

3. The process of claim 1 wherein the reflux to feed molar ratio in the fractionation zone is from about 0.01 to about 0.02.

4. The process of claim 1 wherein the concentrated liquid product stream containing heavy reaction by-products is removed in an amount less than about 0.5 weight percent of the selective hydrogenation reaction zone effluent.

5. The process of claim 1 wherein the butadiene extraction vaporizer is operated at a temperature from about 80° F. to about 200° F. and a pressure from about 40 to about 100 psig.

* * * * *